United States Patent [19]
Rutten et al.

[11] Patent Number: 5,964,793
[45] Date of Patent: Oct. 12, 1999

[54] LEAD INTRODUCER WITH DEFIBRILLATION ELECTRODE AND METHOD OF ATRIAL DEFIBRILLATION

[76] Inventors: Jean Rutten, Persoonstraat 21, Bocholtz; Karel F.A.A. Smits, Gelrestraat, Munstergeleen 6151 JA; Frederic W. Lindemans, Toon Hermanssingel 5, Sittard 6132 BT, all of Netherlands

[21] Appl. No.: 08/667,102

[22] Filed: Jun. 20, 1996

[51] Int. Cl.⁶ ................................................. A61N 1/05
[52] U.S. Cl. ................... 607/119; 604/280; 607/5
[58] Field of Search ................... 607/115, 116, 607/119, 122, 123, 5; 128/642, 656–658, 772; 604/114, 280; 606/129

[56] References Cited

U.S. PATENT DOCUMENTS

| | | | |
|---|---|---|---|
| 4,603,705 | 8/1986 | Speicher et al. | 607/122 |
| 5,044,375 | 9/1991 | Bach, Jr. et al. | 607/122 |
| 5,099,838 | 3/1992 | Bardy | 128/419 |
| 5,115,818 | 5/1992 | Holleman et al. | 607/122 |
| 5,180,376 | 1/1993 | Fischell | 604/282 |
| 5,261,400 | 11/1993 | Bardy | 607/5 |
| 5,366,490 | 11/1994 | Edwards et al. | 607/116 |
| 5,380,304 | 1/1995 | Parker | 605/282 |
| 5,381,790 | 1/1995 | Kanesaka | 128/642 |
| 5,383,922 | 1/1995 | Zipes et al. | 607/122 |
| 5,409,469 | 4/1995 | Schaerf | 604/282 |
| 5,429,130 | 7/1995 | Goldman | 128/642 |
| 5,509,411 | 4/1996 | Littman et al. | 128/772 |
| 5,571,159 | 11/1996 | Alt | 607/122 |

FOREIGN PATENT DOCUMENTS

| | | | |
|---|---|---|---|
| 219608 | 4/1987 | European Pat. Off. | 607/122 |

*Primary Examiner*—William E. Kamm
*Assistant Examiner*—George R. Evanisko
*Attorney, Agent, or Firm*—Harold Patton; Michael J. Jaro

[57] ABSTRACT

There is provided a system and method for treating cardiac arrhythmias such as atrial defibrillation, and in particular a method for providing temporary atrial defibrillation which involves insertion of only one defibrillation lead. A lead introducer is provided having a sheath with an electrode configured around the outside of the sheath and a lumen for receiving therethrough a standard defibrillation lead. After insertion of the introducer into a patient's vein and positioning it so that the introducer electrode is placed within the vein, a defibrillation lead is passed through the introducer lumen. The defibrillation lead carries at least one electrode, suitably an electrode spaced from its distal end so that it can be positioned in the patient's coronary sinus. When the introducer electrode and the defibrillation lead electrode are optimally placed, they are electrically connected to a defibrillation unit for generation and delivery of a defibrillation pulse or pulses across the two electrodes, thereby providing therapy against the atrial fibrillation. In a preferred embodiment, the introducer electrode is a very flexible coil, and is positioned in the patient's subclavian vein; the defibrillation lead electrode is positioned in the patient's coronary sinus. Alternately, the electrode can be any other conductor configuration which provides the desired surface area and flexibility, e.g., a braid or woven wire configuration.

12 Claims, 4 Drawing Sheets

LEAD INTRODUCER WITH DEFIBRILLATION ELECTRODE AND METHOD OF ATRIAL DEFIBRILLATION

BACKGROUND OF THE INVENTION

This invention relates to a lead introducer system and method of atrial defibrillation and, more particularly, to an introducer system for inserting a transvenous endocardial lead for the purpose of achieving atrial defibrillation.

Atrial fibrillation (AF) is one of the most common arrhythmias, and is usually associated with patients of an increased age. About ten percent of patients who are at least 65 years old present with AF. Atrial fibrillation is associated with troublesome symptoms for patients, and also has a significantly adverse influence on the cardiac function. It is also well known that there is an increased risk of embolic events following AF. Accordingly, the increased heart rate associated with AF needs to be controlled. The primary current treatments for AF are the use of anti-arrhythmic drugs, or electric cardioversion. Use of anti-arrhythmic drugs is often associated with potential proarrhythmic effects, especially in patients with already compromised ventricular function. Such a proarrhythmic effect can outweigh the potential benefit of drug administration. On the other hand, transthoracal electrical cardioversion is an extreme therapy, requiring a discharge energy in the range of 50 to 360 Joules. This treatment requires general anesthesia, and serious side effects may occur as a result. Additionally distressing is the fact that there are a substantial number of patients who may fail to being cardioverted externally.

Recently, transvenous cardioversion of atrial fibrillation and other arrhythmias has been demonstrated to be effective. The energies usually necessary to fibrillate in a case of atrial fibrillation are much lower, being in the range of about 1.0 to 5.0 Joules, depending upon a number of factors, particularly the electrode configuration. Electrode configurations that have been tried include the use of different electrodes respectively in the right atrium, right ventricle, arteria pulmonalis, vena cava superior and/or vena cava inferior. The subclavian electrode position has been found to be promising for achieving low defibrillation thresholds. Accordingly, a configuration that has been in use for atrial defibrillation involves one lead with an electrode in the subclavian vein (SCV) and another lead providing an electrode in the coronary sinus (CS). However, for most of these currently used configurations, it is necessary to puncture the vein several times for introducing two leads through the vein so as to position the electrodes for the defibrillation therapy. Alternately, the problem has been addressed by introducing one lead and placing a cutaneous electrode or needle, or temporary indifferent electrode, in the vein incision, a less satisfactory arrangement. The introduction of two leads or a lead and a second electrode is, of course, cumbersome, time-consuming, and costly. Particularly in emergency situations it is desirable to simplify the procedure as much as possible.

There thus exists a significant need in the area of atrial defibrillation, and particularly temporary atrial defibrillation, for a system enabling introduction of only a single transvenous lead to the heart for the purpose of delivering the atrial defibrillation therapy. Such a therapy is needed for patients with, e.g., paroxysmal AF, open heart surgery, or those receiving a pacemaker cardioverter-defibrillator (PCD) type device. In such applications, it is desired to minimize the effort needed to position the required electrodes properly for administering the AF therapy.

SUMMARY OF THE INVENTION

In view of the above, there is disclosed an introducer and introducer system for treating patients with atrial fibrillation, and particularly patients for whom temporary defibrillation is indicated. The system and method of this invention utilize an electrode built into the sheath of an introducer, which introducer electrode is used together with at least one electrode on a transvenous lead which is suitably introduced to position an electrode in the coronary sinus (CS). This system and method provide a less expensive and substantially simpler procedure for providing temporary atrial defibrillation, as well as other forms of cardioversion.

The system of this invention comprises an introducer sheath which is placed into the vein, the sheath having an electrode carried on its periphery, preferably a coil electrode or other conductor configuration. In an exemplary application, the introducer sheath is positioned to place the coil electrode within the subclavian vein (SCV), and a transvenous defibrillation lead is inserted through the introducer and directed to a position where suitably at least one electrode carried on the lead is positioned in the coronary sinus. The SCV electrode on the introducer, and the CS electrode on the lead, are connected to a defibrillator unit, for administration of an atrial defibrillation shock or shocks. In a preferred embodiment, the introducer electrode coil has a large pitch and is made of a very thin diameter wire, and is suitably trifilar, so as to maintain the desirable flexibility of the introducer and the consequent ability to properly position the introducer into the vein.

DESCRIPTION OF THE PREFERRED EMBODIMENTS

The standard method for introduction for an endocardial lead into a patient's vein, as is done in treatment of fibrillation, is well known. An endocardial lead is suitably placed in contact with the endocardial tissue through a venous access, such as the subclavian vein or one of its tributaries. The transvenous endocardial lead offers the advantage that it can be placed into contact with the heart without requiring major thoracic surgery, since it can be introduced into a vein and maneuvered therefrom into contact with the heart. However, the procedure for introducing such a lead into the venous system is a multiple step procedure, and requires the use of what is referred to as an introducer.

Reference is made to U.S. Pat. No. 5,409,469, assigned to Medtronic. Inc., for a discussion of the multiple step procedure used to introduce a transvenous lead into a patient's venous system. In brief, the procedure involves first inserting a hollow needle into a vessel, such as the subclavian vein. A wire guide is then passed through the needle into the interior portion of the vessel, whereafter the needle is withdrawn. An introducer sheath and dilator assembly is then inserted over the wire guide into the vessel, and the assembly is advanced so that the distal end is well within the vessel but the proximal end remains outside of the patient. Next the dilator and guide wire are removed, leaving the introducer sheath in position. The introducer serves the function of providing direct access from outside the patient into the interior of the blood vessel, so that a lead can be passed into the vessel through the sheath and positioned in the heart, or wherever desired. For permanent implant procedures, the introducer sheath is then removed from the body, but this is not necessary for a temporary application.

Figure 1:
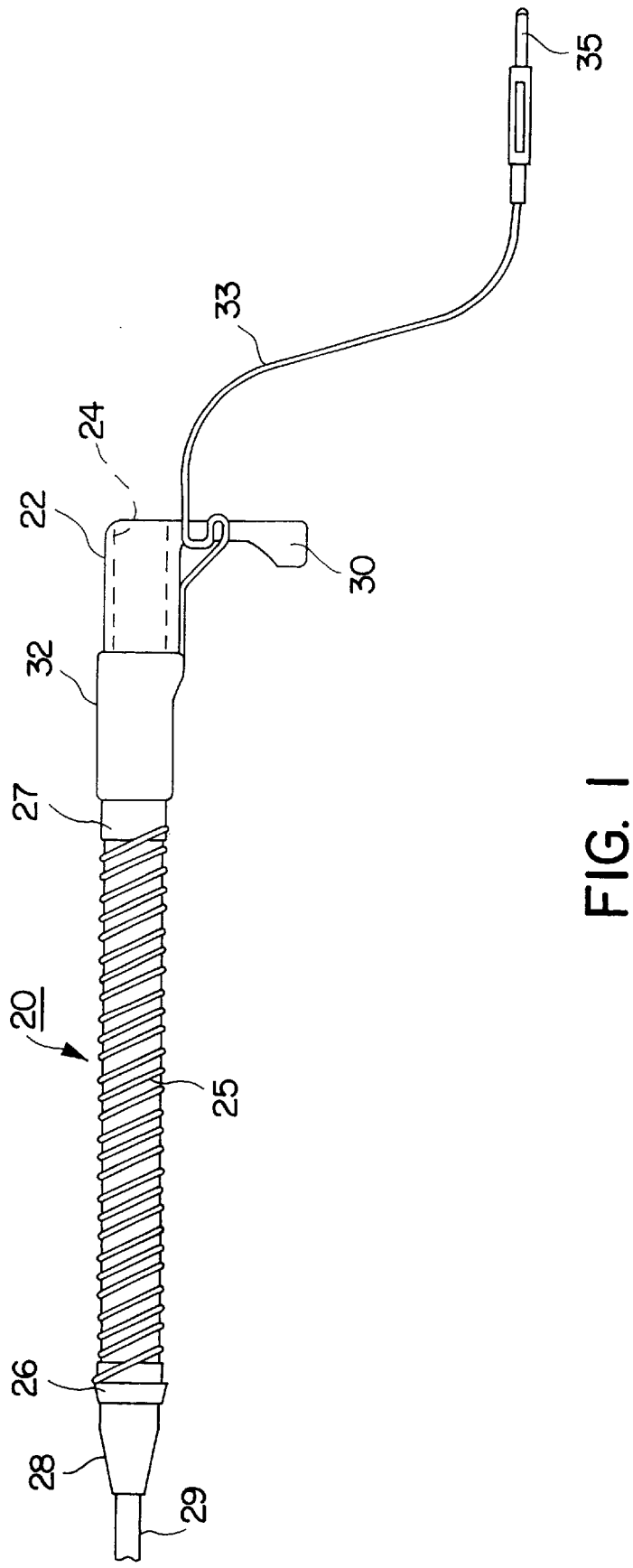
FIG. 1 is a schematic representation of a preferred embodiment of the introducer device of this invention which carries a coil electrode.
Figure 2:
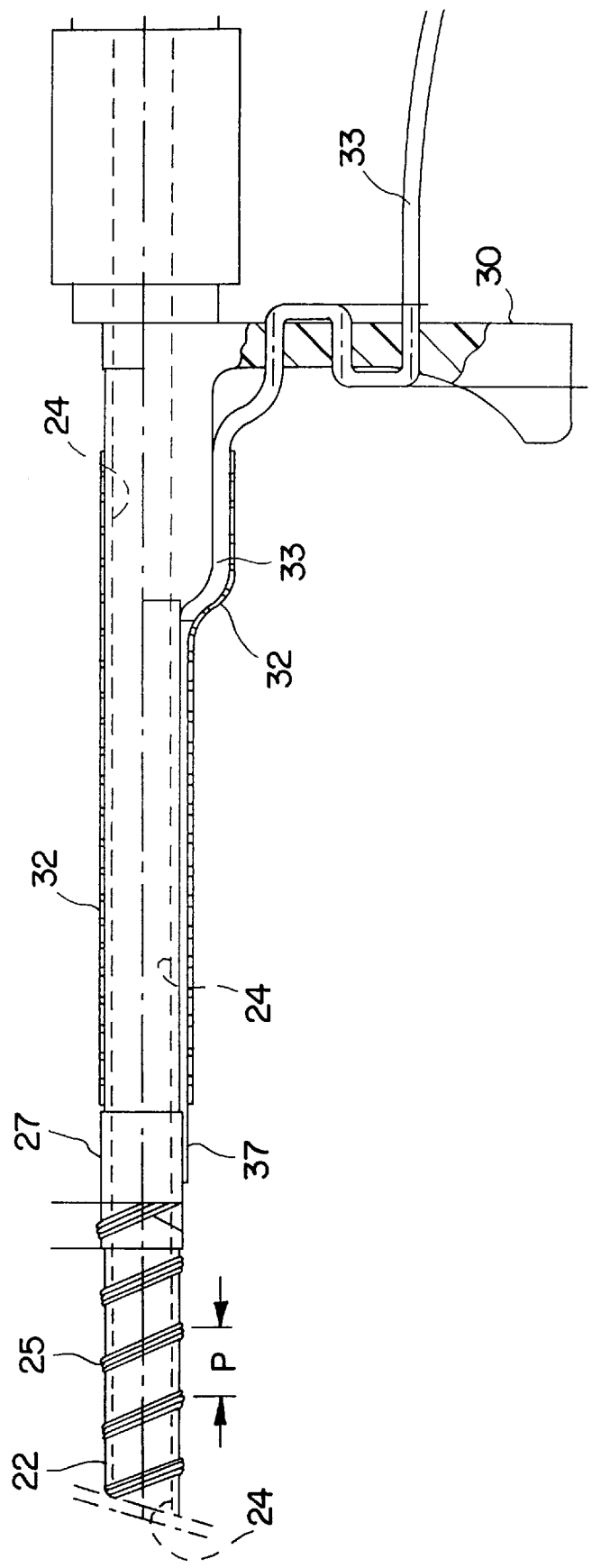
FIG. 2 is an enlarged schematic of a portion of the introducer electrode and the proximal end of the introducer apparatus of this invention.

Referring now to FIG. 1 and FIG. 2, there are shown the component elements of the introducer device of this invention. Introducer 20 has a sheath 22, preferably made of polyurethane or a type of Teflon. The sheath 22 has a lumen indicated at 24 running the length of the sheath. For a preferred embodiment, the lumen is suitable for a size 7 French; the lumen may accept a lead in the size range of 4–8 French. Connected as part of the introducer assembly at the time of placing the introducer into the vein is a dilator, a portion of which is shown schematically at 29. It is, of course, understood that the dilator is removed when the sheath has been placed in the vein, in order that a standard 6 or 7 French lead can be inserted through the 7 French introducer.

An electrically conductive coil 25 is illustrated as being wrapped around the outer diameter of the sheath 22, extending through an intermediate range of the introducer. As shown, the coil is electrically connected to a distal ring 26 and a proximal ring 27. The electrode coil is multifilar, preferably trifilar, and each electrode wire is separately spot welded to each ring at at least 3 places, as indicated at 37 in FIG. 2. The electrode rings may be covered with a suitable glue, to prevent any rough spots. Conductor 33, being suitably a wire covered by suitable compatible insulation material, has a distal end spot welded to ring 27, and a proximal end which connects to pin 35, pin 35 being adapted for plugging into a pulse generator, e.g., an external defibrillator device or a PCD-type device for delivering an anti-AF shock or shocks. Introducer 20 has a handle 30 at its proximal end, and an outer tubing, preferably silicon rubber, illustrated at 32, which covers the sheath and conductor 33. Tubing portion 32 may be variable in length, the typical length being about 2.5 cm. However, this length may be extended for about another 5 cm, for applications where it is desired to adjust the coil electrode 25 further into the vein.

Returning to the electrode coil 25, it has a nominal coil length of about 12 cm. This length is variable, and preferably is within the range of 10–14 cm; however, it can be less than 10 cm, or greater than 14 cm. The coil is trifilar wound, each wire having a thickness nominally of 0.2 mm, an outside diameter of 3.10 mm, and a total wire length of 120 cm. The coil wire is suitably a flexible platinum/iridium wire, with a large pitch on the order of 2–5 mm nominal, with the spacing between filars being nominally about 1 mm. With this design, there is provided a very flexible and low resistance coil electrode. The coil may also be made of stainless steel or another biocamptible, conductive material. The coil inner diameter is just slightly larger than the outer diameter of the sheath, enabling positioning of the coil easily over the sheath without reducing the inner diameter of the 7 French introducer, and without presenting any significant gap between the coil and the introducer. The outside diameter of the introducer with the coil electrode preferably does not exceed 3.7 mm, so that a splitable 11 French sheath can slide easily over the introducer.

While the preferred embodiment of the lead introducer has been illustrated as having a coil electrode, the introducer electrode may have other configuration. For example, the electrode may be a braided or woven structure, presenting a different electrode configuration. As with the coil embodiment, any alternate electrode configuration presents a very flexible, low resistance electrode. As used herein, the term "conductor configuration" includes the coil embodiment, as well as braided, woven, "basket" and other configurations.

Figure 3:
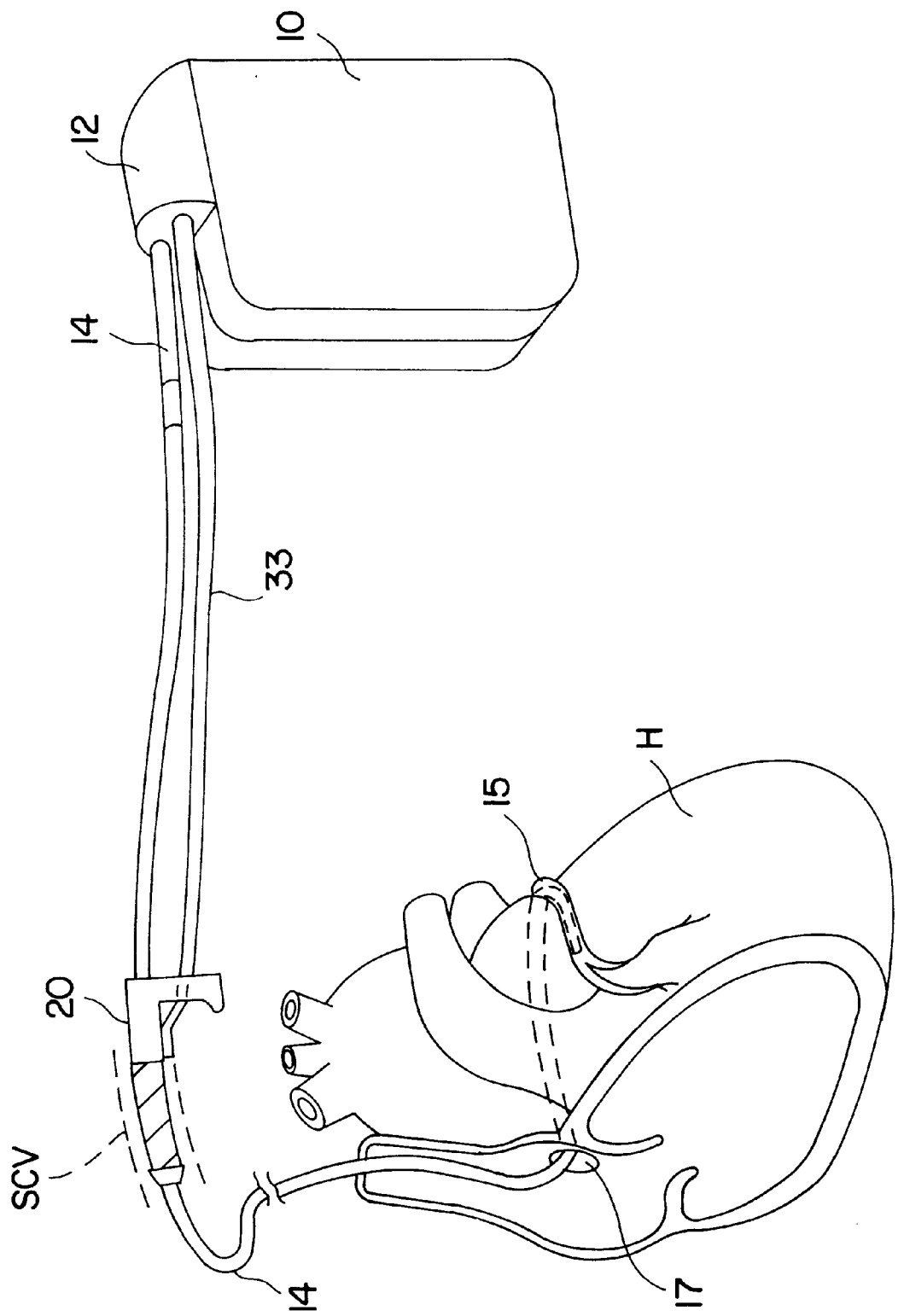
FIG. 3 is a representation of the system of this invention, showing the introducer inserted into the subclavian vein and the defibrillation lead introduced so that an electrode is positioned in the coronary sinus.

Referring now to FIG. 3, there is illustrated the system combination of a generator unit 10, defibrillator lead 14 and introducer 20, illustrating the system in place for applying therapy for an AF condition. Pulse generator unit 10 is any suitable device, either an external device or an implantable device, for generating appropriate defibrillation shock therapy. For example, a PCD type device such as made by Medtronic, Inc., may be used. As used herein, the term shock may represent a single defibrillation shock, coupled shock pulses, or any other known form of cardioversion pulse sequence. A connector block 12 receives the proximal end of defibrillator lead 14, as well as pin 35 on the proximal end of conductor 33 and which connects to the introducer coil electrode. As shown, the introducer 20 is positioned within the subclavian vein (illustrated by dashed lines marked SCV). Lead 14 has been manipulated through an opening 17 into the coronary sinus, and is illustrated a having an electrode 15 positioned within a coronary sinus of the heart H. With this arrangement, the therapy can be administered between the introducer electrode 25 and the CS electrode 15. It is to be understood that while this is a preferred positioning of the electrodes, other electrode positions may be used, for treating both AF and VF, as well as other types of arrhythmias. For example, the defibrillation electrode need not be placed in the heart, but can be placed near to or in the proximity of the heart. As used herein, the phase "in the proximity of the patient's heart" includes within the heart. Thus, the electrode could be placed in the right ventricle or right atrium; or in the vena cava inferior or superior. Although a primary application of the invention is in treating AF, it is noted that the invention is not so limited and is applicable for other uses, and to the treatment of other types of arrhythmias, including VF. The introducer can be used as the indifferent electrode for temporary unipolar pacing, as a reference electrode for recording unipolar cardiac electrograms, or as one of the electrodes used during defibrillation threshold testing for defibrillator implantation.

Figure 4:
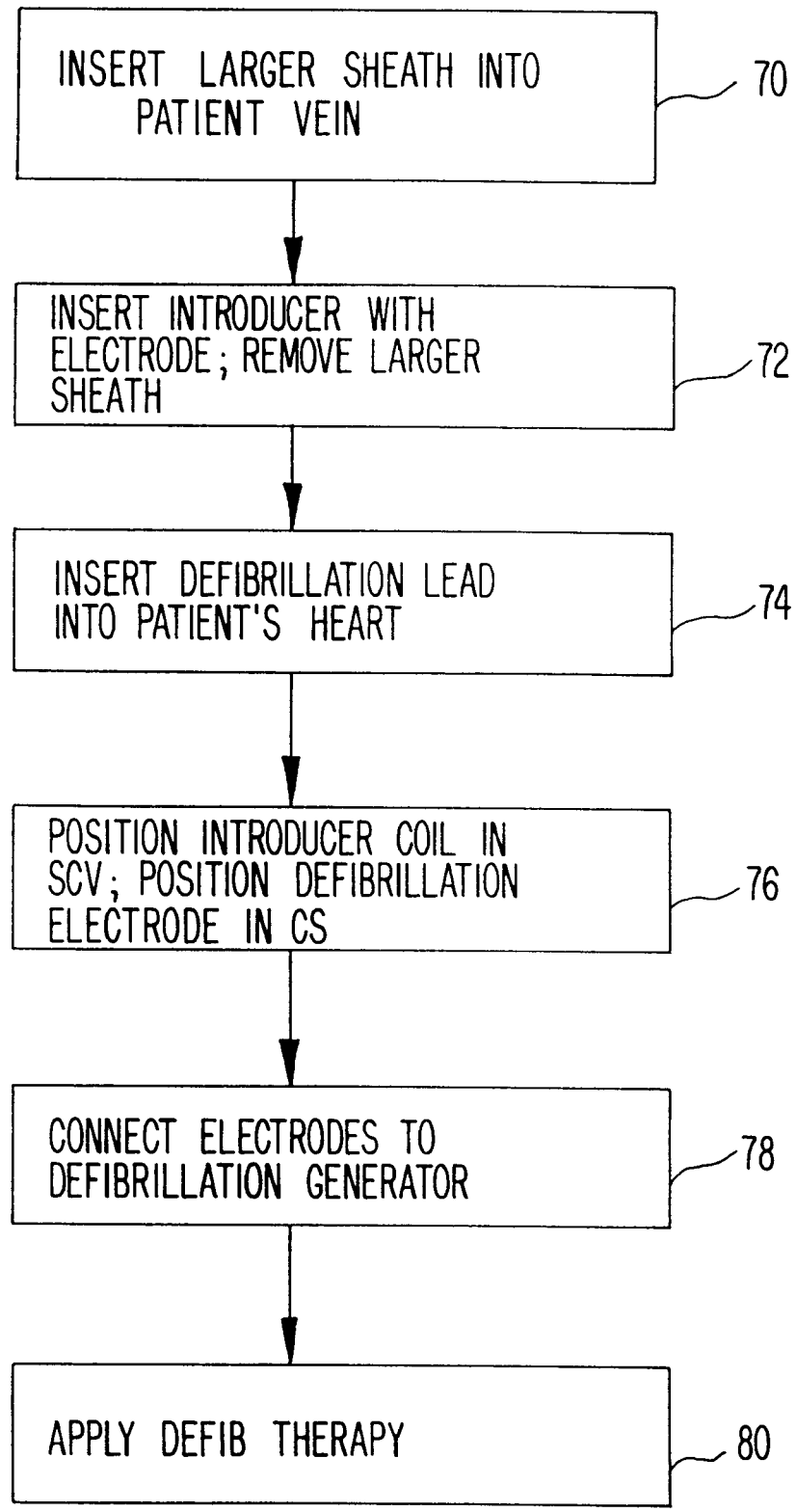
FIG. 4 is a flow diagram illustrating the primary steps in carrying out the method of this invention.

Referring now to FIG. 4, there is shown a very general flow diagram which illustrates the primary components of the method of using the introducer of this invention for the purpose of applying defibrillation therapy. It is to be understood that this flow diagram does not represent all of the steps of introducing the defibrillation lead into the patient's venous system and readying the patient for the therapy, but is intended only to present the primary steps carried out by the method of this invention. At 70, a larger introducer sheath, preferably 11 French, is inserted into the patient's vein. The splitable introducer sheath is large enough to fit the lead introducer, but small enough to prevent blood leakage. For each size lead introducer, e.g., 4–8 French, a corresponding size splitable sheath is used. The larger splitable sheath is used to minimize any problem upon insertion of the introducer 20, due to the coil electrode 25 which is on the outside of the sheath 22. In this regard, it is to be noted that the coil may be embedded into the sheath to provide a smooth outer surface, in which case the larger sheath would not be required. For the embodiment of FIGS. 1 and 2, the thin diameter of the trifilar wires minimizes the effect of the coil on the introducer outside surface.

As illustrated at 72, the introducer with the electrode is inserted into the patient's vein, following which the larger sheath, which is splitable, is removed from the patient. Although not illustrated, the guide wire and dilator would also be removed. At 74, there is illustrated the step of inserting the defibrillation lead, carrying the defibrillation electrode, into the patient's heart so as to position electrode 15 at a suitable location, e.g., in the CS. Although the invention has been illustrated showing just one electrode on the defibrillation lead, it is to be understood that this lead may have other electrodes, not shown. Following this, the introducer electrode coil is positioned in the patient's subclavian vein, and the defibrillation electrode is positioned in the coronary sinus, as illustrated at 76. When the positioning has been done optimally, the electrodes are connected to the defibrillation generator, as illustrated at 78. At this time, the system is fully in place, and the defibrillation therapy is applied as indicated at 80. Of course, the introducer is subsequently removed from the subclavian vein.

There has thus been illustrated an improved introducer device and system, and method for providing therapy for cardiac defibrillation. In particular, the invention provides a temporary system for quickly defibrillating the atrium, which system and method require the insertion of only one lead into the patient's heart. It is to be noted that for the use of a transvenous lead, an introducer has to be used in any event. This invention utilizes the introducer to carry an electrode, thereby removing the necessity of inserting a second lead. The invention further provides an embodiment which does not appreciably decrease the flexibility of the introducer, which flexibility is very important for good lead insertion. The introducer can be used for a variety of pacing and cardioversion procedures, as well as for non-cardiac procedures, e.g., obtaining access to another vein such as a femoral vein in the groin.

What is claimed is:

1. A system for providing therapy in response to atrial fibrillation or other cardiac arrhythmias, said system comprising:

an introducer, said introducer having a lumen therethrough for passage of a lead, said introducer further having an introducer electrode on its periphery and positioned for placement in a patient's vein when the introducer is inserted into said patient's vein said introducer electrode having means for minimizing any decrease in introducer flexibility contributed by the introducer electrode;

a defibrillation lead for insertion through said introducer lumen, and having a defibrillation lead electrode thereon placed for positioning in the proximity of the patient's heart;

a defibrillation device, having output terminals for delivering a defibrillation shock; and connecting means for connecting said introducer electrode and said defibrillation lead electrode to said defibrillation output terminals, whereby defibrillation therapy can be applied.

2. The system as described in claim 1, wherein said introducer comprises a sheath having an outer wall and an inner wall, said inner wall defining said lumen, and wherein said lumen has a diameter having a size within the range of 4–8 French so as accommodate a lead having a size within the range of 4–8 French.

3. The system as described in claim 2, wherein said introducer electrode is a coil positioned on the outer wall of said sheath, and wherein said introducer comprises an electrical conductor having a connecting pin at its distal end and having its other end electrically connected to said coil.

4. The system as described in claim 3, wherein said coil has a length in the range of about 10–14 cm.

5. The system as described in claim 4, wherein said coil has a spacing between turns of about 0.2 to 0.4 cm.

6. The system as described in claim 4, wherein said coil has an outer diameter and a spacing such that it is very flexible.

7. The system as described in claim 1, wherein said difibrillation lead electrode comprises a conductor configuration.

8. The system as described in claim 1, wherein said introducer has a distal tip and a proximal end, a handle attached to said proximal end, and a distance in the range of 2.5–7.5 cm between said difibrillation lead electrode and said handle.

9. A method of applying a therapy for a patient with atrial fibrillation, said method employing a pulse generator capable of producing shock pulses for treatment of atrial fibrillation, said method comprising:

inserting an introducer into a vein leading to the patient's heart, said introducer having an outside wall with a introducer electrode thereon, and positioning said first electrode in said patient vein;

inserting a lead through said introducer, said lead having at least one lead electrode thereon, and positioning said lead so that said at least one lead electrode is positioned in the proximity of the patient's heart;

electrically connecting said introducer electrode and said lead electrode to said pulse generator; and applying an anti-atrial fibrillation pulse across said introducer electrode and said lead electrode, so as to provide defibrillation therapy to said patient.

10. The method as described in claim 9, comprising placing said introducer electrode in the patient's subclavian vein, and placing said fibrillation lead electrode in the patient's coronary sinus.

11. The method as described in claim 9, further comprising selecting a location for placement of said introducer electrode, and adjusting the insertion of said introducer so as to position said introducer electrode at said selected position.

12. The method as described in claim 9, comprising first introducing a first sheath, said first sheath having a larger lumen of a size sufficient to receive therethrough at least said introducer, selecting said introducer of a size within the range of 4–8 French, and after introduction of said first sheath inserting said introducer through said larger lumen and into said patient's vein.

* * * * *